US00RE36666E

United States Patent [19]

Honkanen et al.

[11] E Patent Number: Re. 36,666

[45] Reissued Date of Patent: Apr. 18, 2000

[54] MICRO-INSTRUMENT

[75] Inventors: George P. Honkanen, deceased, late of North Scituate; by Roger M. Burke, legal representative, Weston; Roger M. Burke, Weston; Paul C. Weaver, Bridgewater, all of Mass.

[73] Assignee: TNCO, Inc., Whitman, Mass.

[21] Appl. No.: 08/319,434

[22] Filed: Oct. 6, 1994

Related U.S. Patent Documents

Reissue of:

[64] Patent No.: 5,152,780
Issued: Oct. 6, 1992
Appl. No.: 07/531,785
Filed: May 31, 1990

[51] Int. Cl.[7] ..... A61B 17/28

[52] U.S. Cl. ..... 606/205; 606/174; 128/751

[58] Field of Search ..... 606/51, 52, 174, 606/205–211; 128/750–755; 604/22

[56] References Cited

U.S. PATENT DOCUMENTS 4,662,371 5/1987 Whipple et al. .

*Primary Examiner*—Michael Buiz
*Assistant Examiner*—William Lewis
*Attorney, Agent, or Firm*—Stephen Y. Chow; Perkins, Smith & Cohen,LLP

[57] ABSTRACT

A microsurgical instrument with opposing jaws rotatable relative to one another using a pivot integral to a frame comprising one jaw for rotating the other jaw and a linkage to push one jaw rotatably towards the other jaw wherein a distal-most surface of that jaw pushes against a surface of jaw to be moved.

11 Claims, 6 Drawing Sheets

MICRO-INSTRUMENT

Matter enclosed in heavy brackets [ ] appears in the original patent but forms no part of this reissue specification; matter printed in italics indicates the additions made by reissue.

BACKGROUND OF THE INVENTION

The present invention relates to micro-instrumentation, i.e. articulating hand held instruments used in micro-surgery, electronic micro-assembly and like applications, for grasping, cutting, punching out, probing, etc. The instruments can comprise scissor-handle-actuators, so-called cigar handle linear or rotary activators, or other actuators, with push or pull force application design modes.

The following discussion of the invention focusses on instruments required for endoscopic usage (minimally invasive procedures) and more particularly punches, scissors and graspers used in temporal-mandibular joint (TMJ) surgery. However, the invention is also applicable to other surgical instruments and non-surgical instruments.

Recent generations of enhanced miniaturization of endoscopic instruments have encountered the structural limits of thin cross-sections. As the tip area of such instruments is reduced, the likelihood of breakage and/or the need to reduce applied force becomes evident. The high strength and toughness of advanced metal alloys have not overcome this problem.

It is a principal object of the invention to provide micro-instruments of the classes described above of superior strength. It is a further object of the present invention to provide micro-instruments of the classes described above with reduced tip cross-section dimensions with a rigidity, stability and low vulnerability to breakage heretofore found only in larger instruments.

It is a further object of the present invention to provide micro-instruments of the classes described above with a characteristic that upon a breakage while in use, there is minimal probability of pieces separating from the main body of the instrument.

It is a further and related object of the invention to enable a new level of miniaturization of such instruments and to enable the existence of interlocking type graspers at such new level (as well as punches, scissors and other cutters).

It is a further object of the invention to achieve the previous objects with ease of manufacturability.

SUMMARY OF THE INVENTION

The objects of the invention are realized through the invention's provision of the said instruments in a miniaturized form with articulating handle means (of rod or scissors grip forms or other forms) and elongated probe means extending therefrom, with an elongated actuating linkage portion and a tip portion at the probe end distal from the handle.

The handle portion is, per se, of conventional form.

The actuating linkage preferrably comprises a shaft fixedly mounted from the handle, with a longitudinal groove or hole receiving an actuating rod and mounting the tip portion at the distal end of the shaft.

The tip portion comprises an assembly of relatively moveable components usually defined as an inner tip and outer tip. As applied to a surgical punch, the inner tip literally moves within an envelope largely defined by an outer tip. As to scissors and the like the nomenclature is more arbitrary. Generally, the "inner" tip moves while the "outer" tip is stationary although in some applications the reverse or both can move. The tip assembly is operated to excise tissue in bits, to separate one piece of tissue from another, to grasp and/or manipulate and/or remove particulate matter. The tip assembly has a pivotal mounting with a fixed shaft extension of the outer tip integrally formed therewith. The articulating inner tip has a groove seating on the shaft extension to define the pivotal mount. An actuating linkage extends from an actuating system in the handle through an elongated channel of the probe and terminating in a connection at the inner tip offset from the pivotal mount to provide a levering articulation motion to the inner tip forward and back between 'upper' and 'lower' positions. In case of breakage in use, each of the inner and outer tip retains its basic shape and neither generates small break-off pieces. Further, the inner and outer tip retain their assembly to each other and assembled to the probe relationships and a significant degree of their operability.

The invention accommodates the direct articulating drive to the inner tip as well as related actions of proper use, e.g. twisting and pulling or pushing of the instrument as a whole, and improper uses.

Positive stops are provided to prevent the inner tip from escaping from its nested relation with the outer tip.

The integral pivot extension of the outer tip which forms the pivot mount preferrably has an hour-glass shape which does not weaken the adjacent outer tip wall(s), but rather enhances strength and rigidity of the same. The integral pivot enables thinner wall sections of the outer tip and shaving the design of 'upper' and 'lower' edges (hereinafter shown) of the outer tip to be closer to the pivot center and maximize engagement of tissue or other material or objects to be grasped.

Other objects, features, and advantages will be apparent from the following detailed description of preferred embodiments taken in conjunction with the accompanying drawing in which:

BRIEF DESCRIPTION OF THE DRAWINGS

In FIG. 1 the inner tip is shown in the partially open position with an adjacent arrow indicating the relative range of motion.

FIG. 3 shows the handle and front end assembled in open position.

DETAILED DESCRIPTION OF PREFERRED EMBODIMENTS

Figure 1:
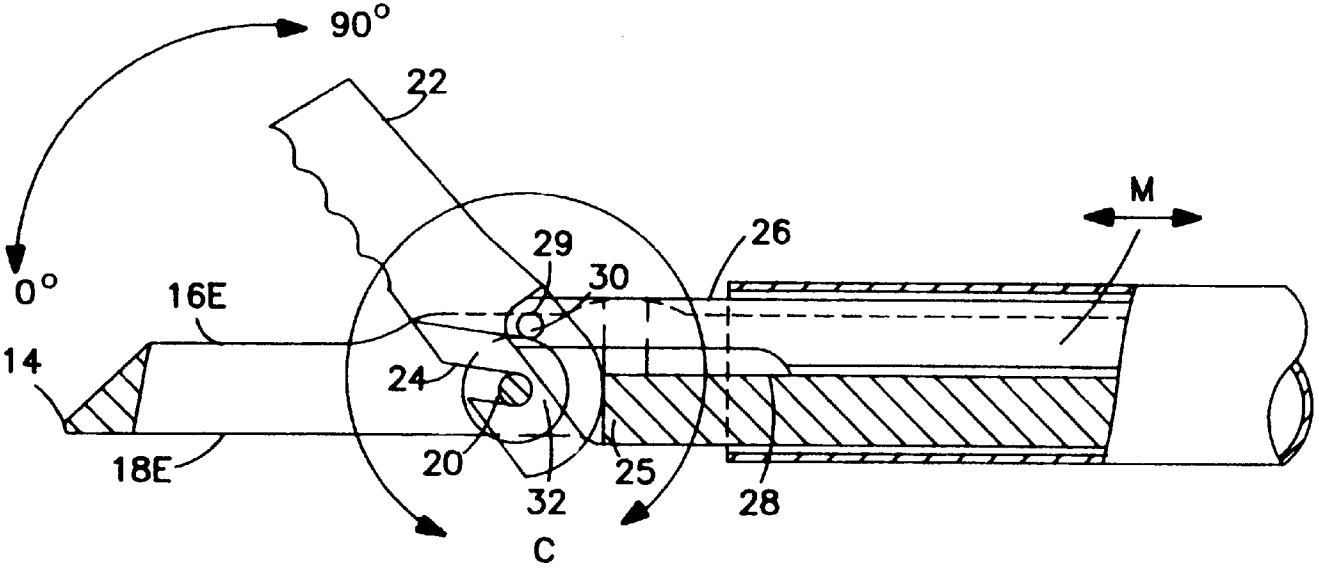
FIGS. 1 and 2 are side and top views of a probe end of a preferred embodiment of the invention applied to a punch utilization with a supplementary diagram (FIG. 1A showing the relative position of fixed and moveable pivots). A cross-section partial top view FIG. 1B showing fixed pivot detail is based on a section taken as indicated by arrows D—D in FIG. 1A. A sectioned assembly portion FIG. 2A showing moveable pivot detail is based on a section per arrows E—E in FIG. 1A. An additional sectioned assembly, FIG. 2B, displays the inner tip positioned within the outer tip and shows the moveable actuator link nested in the inner tip recess. This view is based on section F—F of FIG. 1A.
Figure 2:
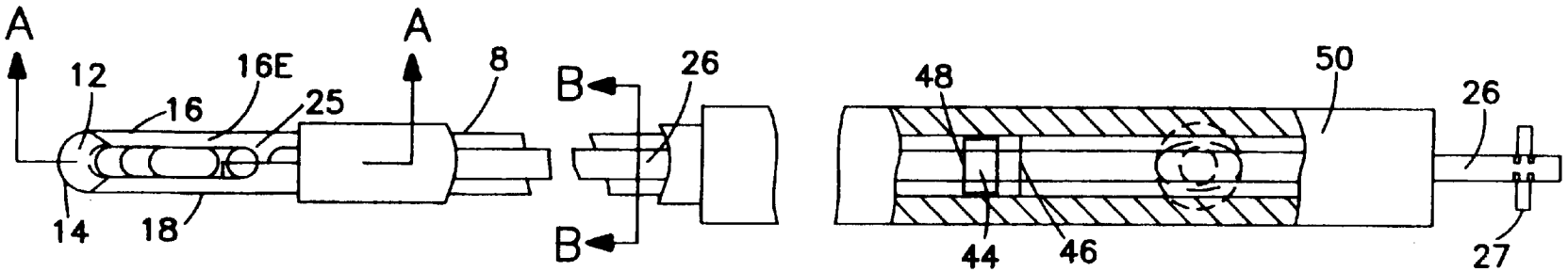

The side view/top view assembly drawings of FIGS. 1–2 (and ancillary views FIGS. 1A, 1B, 2A, 2B and 2C including sections and views taken as indicated at A—A in FIG. 2 for FIG. 1, B—B for FIG. 2C, View C in FIG. 1 for FIG. 1a, D—D and E—E of FIG. A for FIGS. 1B and 2A and F—F of FIG. 1A for FIG. 2B) show an endoscopic punch of a type used in TMJ surgical procedures. The punch has an elongated probe 8 (FIG. 2) with an outer tip 12 of U-shape form with an end 14 and sidewalls 16 and 18 with upper and lower cutting edges 16E and 18E (FIG. 1) and an integral pivot 20 of essentially hourglass form integrally formed with and bridging the walls 16 and 18. An inner tip 22 is mounted on the pivot for rotation as indicated by the double arrow shown in FIG. 1 between an open position (FIG. 1) and a closed position nested within the outer tip. A channel or slot 24 of the inner tip seats on the integral pivot of the outer tip. The channel is shaped with a negative hourglass at its base to conform to the positive hourglass form of the integral pivot 20. The internal centerlines of the positive and negative hourglass forms are coincident. The inner tip's range of arcuate movement brings its upper face to bear on surface 25 of the outer tip. Ramp surface 25 is dimensioned to allow necessary opening rotary motion, but restrict disengagement linear motion of the pivot elements.

The upper portion of the inner tip, above the channel, has a cross-hole 29. This cross hole accommodates a pivot 30 that is an integral pivot extension of a linearly moveable actuating link 26, moveable as indicated by arrow M, riding in a channel 28 and coupled to the inner tip by said pivot 30 that passes through hole 29 in the tip, to drive the inner tip between end positions.

The inner tip has a cut out recess 32 to accommodate the rounded end of link 26. As shown in FIGS. 2B, 2A, 1A and 1 the linear movement of link 26 is transmitted via pivot 30 to the inner tip to move the inner tip through an arc of up to 90 degrees. The inner tip recess includes a front wall 34 that absorbs part of the actuating force applied through link 26 as inner tip 22 is moved counter clockwise against resistant tissue.

Figure 3:
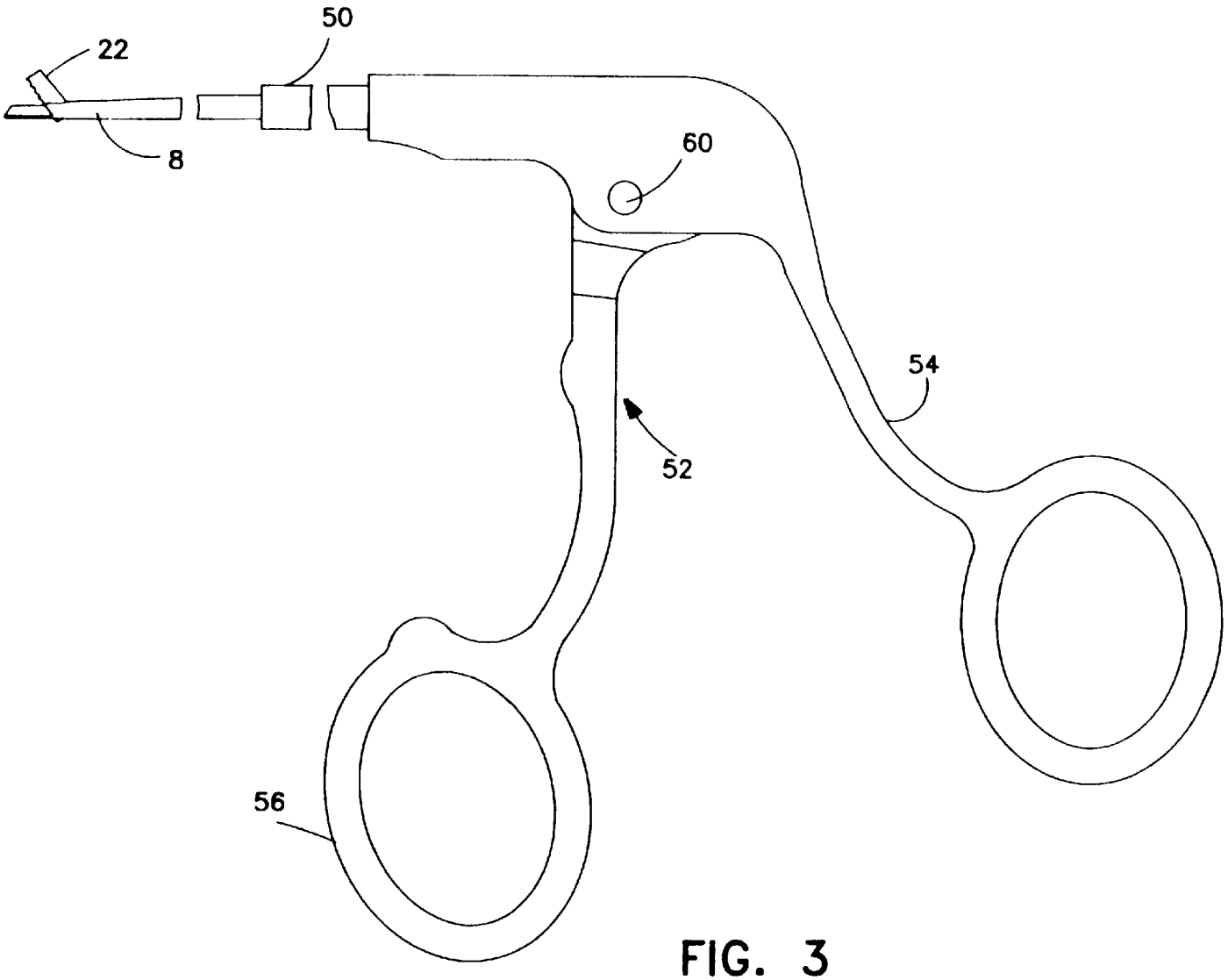
FIGS. 3 and 3B are side views of the instrument's handle portion in open and closed positions.
Figure 3A:
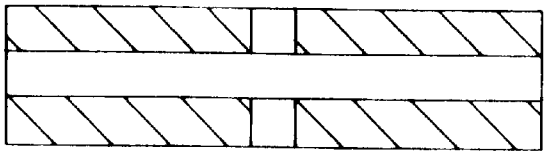
FIG. 3A displays perpendicular slots which retain the actuator and drive pin assembly in the handle and is based on arrows G—G in FIG. 3B.
Figure 3B:
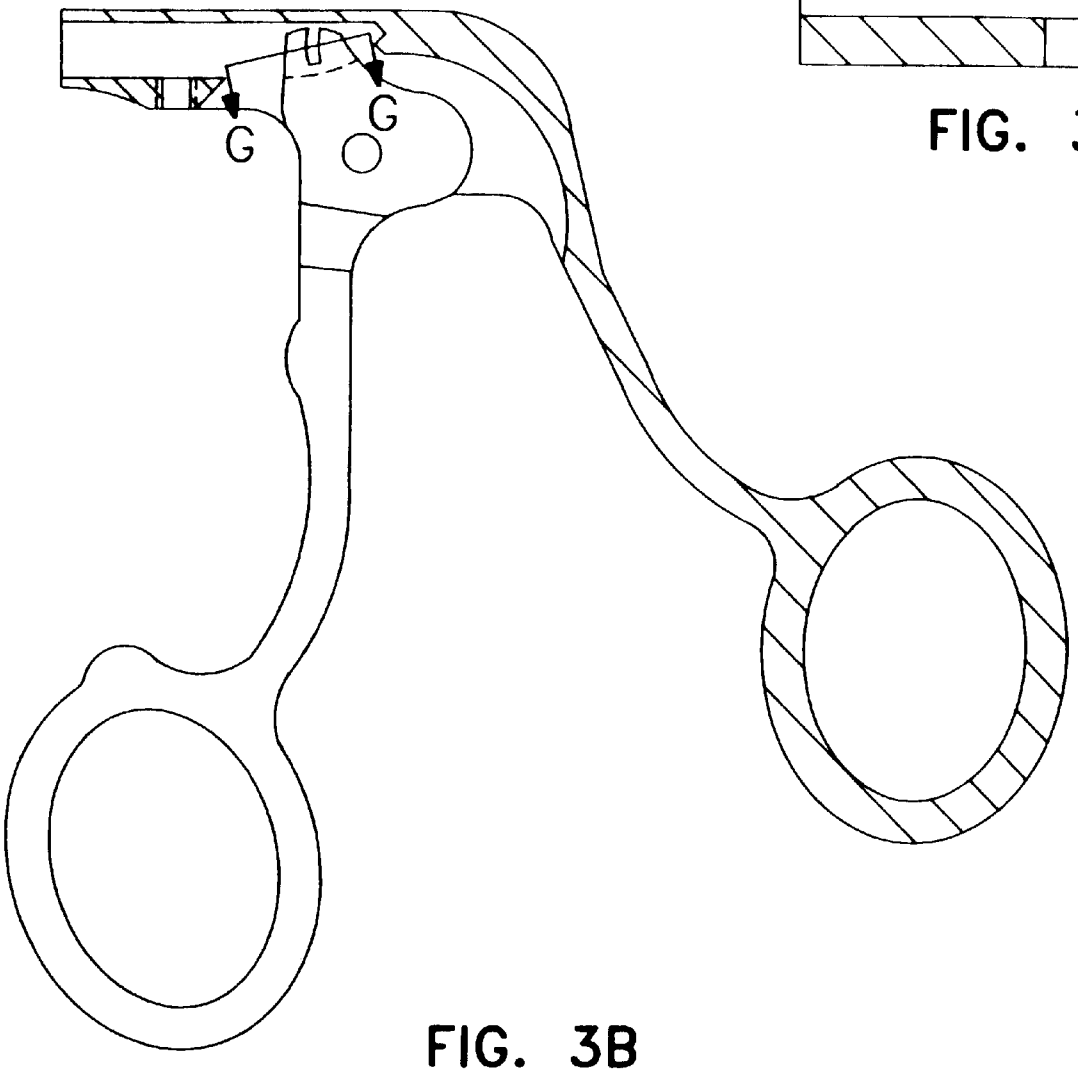

At the handle end, stopping is also controlled by a stop block 44 (FIG. 2) on link 26, moveable for distance M between stop faces 46 and 48 of a wide cutout or slot in the bottom of channel 28. A bushing 50 carries probe 8. The bushing is, in turn, encased in a handle assembly 52 (FIG. 3) comprising a thumb loop 54 and a finger loop 56 pivoted at fulcrum 60. The top of the finger loop above the fulcrum has an axial slot 56-1 (FIG. 3A) and cross slots 56-2, 56-3 forming a fork to receive a cross pin 27 (FIG. 2) through the actuating linkage, thus allowing movement of the finger loop to impart driving force M to the actuator linkage.

Figure 4:
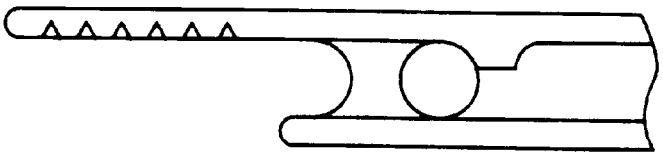
FIG. 4 and 5 show top views of outer tip variants for the scissor and grabber useage embodiment respectively.
Figure 5:
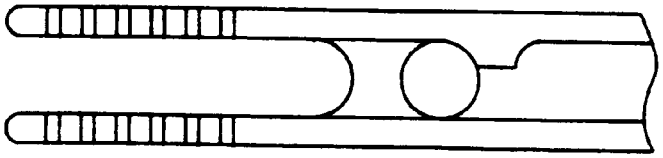

FIG. 4 is a partial top view of the outer tip end 4–12 of an alternative scissors embodiment with side walls 4–16 and 4–18 bridged by an integral pivot 4–20, exemplifying the strengthening ability of this basic pivot. An "inner" tip mounts on the pivot in the same manner as shown in FIGS. 1 and 2. FIG. 5 is a partial top view of the outer tip end 5–12 of an alternative grabber embodiment with side walls 5–16 and 5–18 bridged by an integral pivot 5–20. An "inner" tip mounts on the pivot in the same manner as shown in FIGS. 1 and 2.

Figure 1A:
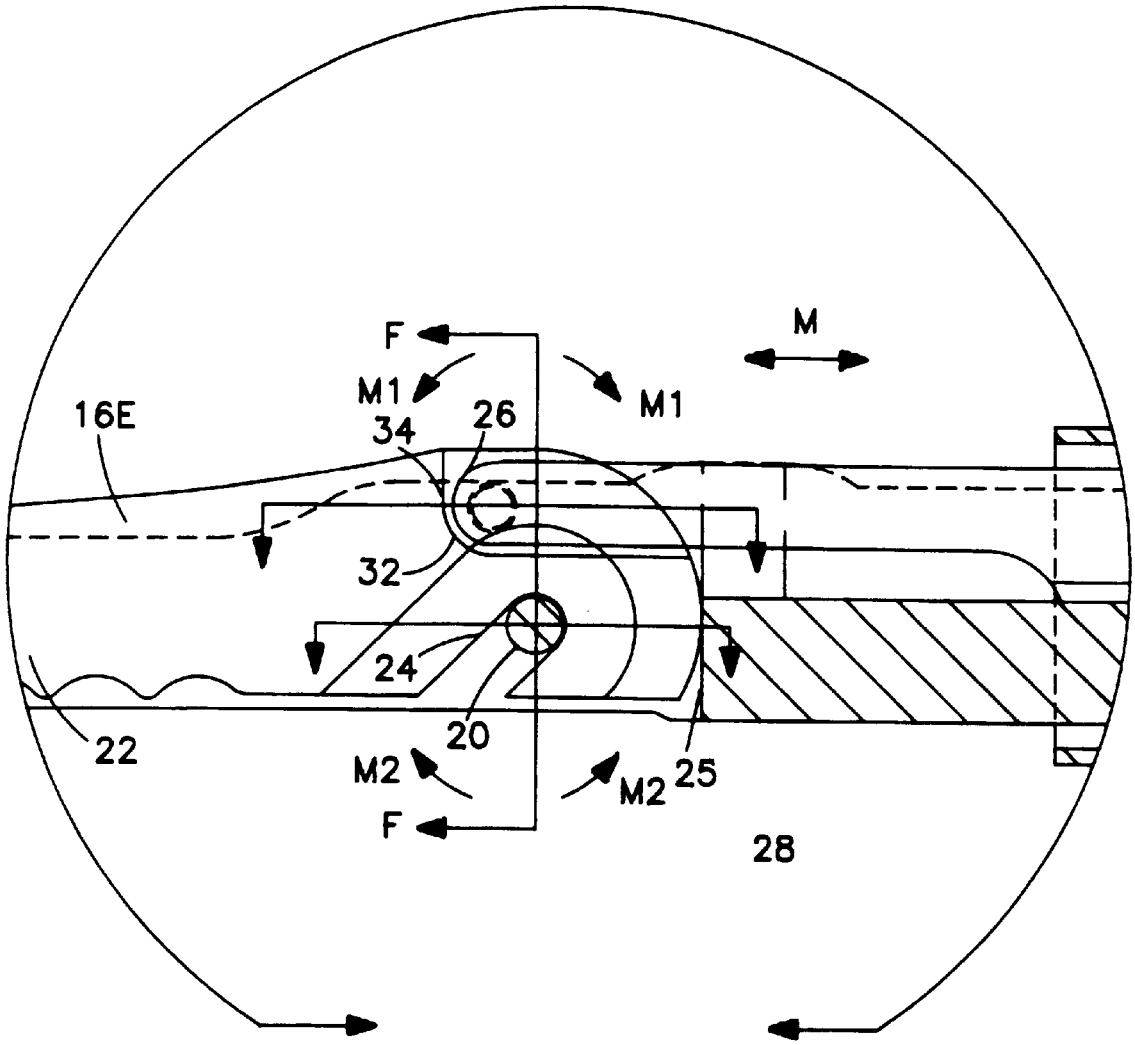
Figure 2B:
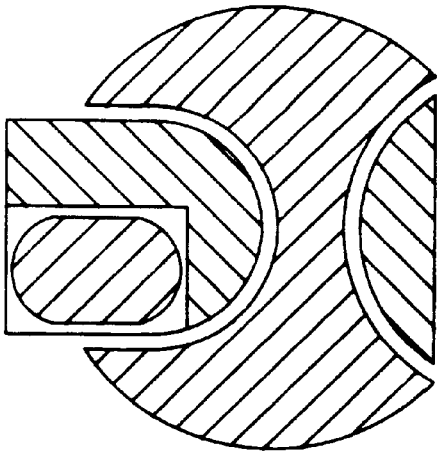
FIG. 2C shows the moveable actuator link nested in the outer tip slot and is indicated by arrows B—B in FIG. 2.
Figure 2A:
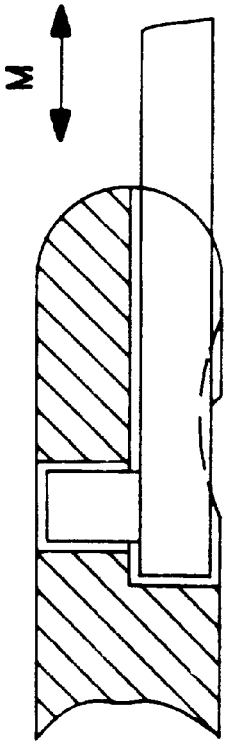
Figure 1B:
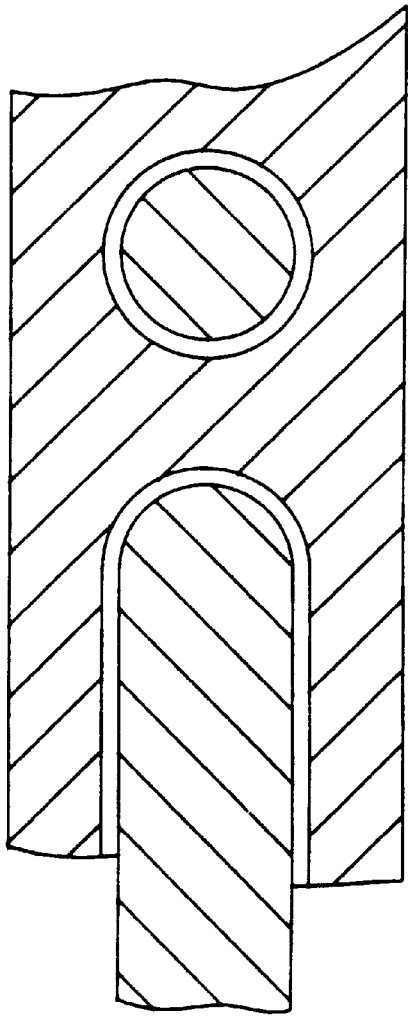
Figure 2C:
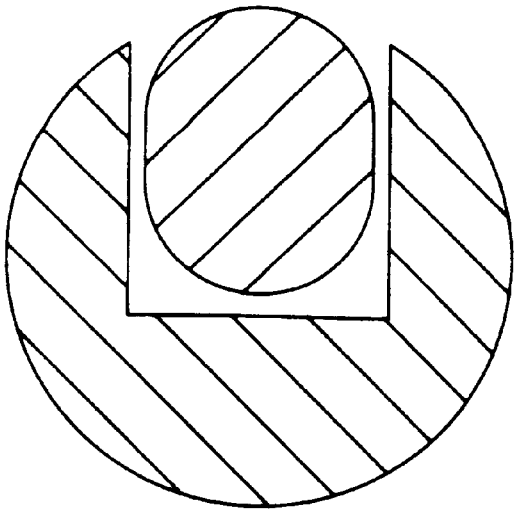

In manufacture, the integral pivot 20 can be made by profiling with a ball end mill cutter into the metal stock of a solid outer tip blank, the cutter being advanced in the directions indicated by arrows M1 and M2 in FIG. 1A. The cut-out area up to surface 25 allows entry of a cutter advanced as indicated by arrow M2 and also allows for inner tip 22 assembly/disassembly with respect to outer tip 12 and pivot 20.

The machine integral pivot shares the metallurgical and strength/toughness characteristics of side walls 16 and 18 of the outer tip 12, whereas welding and other attachment methods would alter and undermine such characteristics within a pivot-tip assembly. The machined integral pivot has, as a natural part of its design, a strength enhancing fillet form at its joinders with the side walls which would not be feasible in a micro-welded construction.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A miniature articulated tip tool for micro-surgical, medical and like uses, comprising:

(a) means defining an articulated tip with at least one pivotable element and a sole pivot element therefor with a range of movement of said tip between extended and retracted positions for effecting selective user controlled pivotal working movements, the said tip defining means comprising at least one fixed wall with an extension thereof formed together in one piece and serving as said pivot element;

(b) means defining a user control handle-actuating system; and (c) means defining an elongated linkage between the handle-actuating system and the articulable tip pivotable member and a channel including such elongated linkage.

2. The tool of claim 1 wherein the tip has a construction of two side walls with said pivot constituting a one piece extension of both.

3. The tool of claim 2 wherein said sidewalls are essentially parallel and the one-piece pivot has essentially an hour glass form.

4. The tool of claim 1 wherein said pivotable element has a hook opening conforming to the pivot.

5. An endoscopic surgical instrument, comprising:

(a) means defining an articulated tip with at least one pivotable element and a sole pivot element therefor with a range of movement of said tip between extended and retracted positions for effecting selective user controlled pivotal working movements, the said tip defining means comprising at least one fixed wall with an extension thereof formed together in one piece serving as said pivot element, and the one-piece pivot having essentially an hour glass form;

(b) means defining a user control handle-actuating system; and (c) means defining an elongated linkage between the handle-actuating system and the articulable tip pivotable member and a channel including such elongated linkage.

6. A grasper for micro-surgical, medical and like uses, comprising:

(a) means defining an articulated tip with at least one pivotable element and a sole pivot element therefor with a range of movement of said tip between extended and retracted positions for effecting selective user controlled pivotal working movements, the said tip defining means comprising at least one fixed wall with an extension thereof formed together in one piece serving as said pivot element;

(b) means defining a user control handle-actuating system;

(c) means defining an elongated linkage between the handle-actuating system and the articulable tip pivotable member and a channel including such elongated linkage.

*7. A miniature articulated tip tool assembly comprising:*

*(a) means defining an articulated tip with at least one pivotable element and a sole pivot element therefor with a range of movement of said tip between extended and retracted positions for effecting selective user controlled pivotal working movements;*

*(b) means defining a user controlled handle-actuating system; and*

*(c) means defining an elongated linkage between the handle-actuating system proximally and the articulable tip pivotable element distally and a channel medially including such elongated linkage such that a distal-most surface of said linkage transmits force directly to a surface of said articulable tip pivotable element to pivot said pivotable element to move said tip into said extended position.*

*8. The tool of claim 7 wherein said tip defining means comprises at least one fixed wall with an extension thereof formed together in one piece and serving as said pivot element.*

*9. The tool of claim 8 wherein the tip has a construction of two side walls with said pivot constituting a one piece extension of both.*

*10. The tool of claim 9 wherein said sidewalls are essentially parallel and the one-piece pivot has essentially an hour glass form.*

*11. A medical instrument comprising:*

*a tubular extension having a longitudinal axis, a distal end and a proximal end;*

*a movable end effector pivotally attached by a pivot to said distal end of said tubular extension; and*

*a drive member located within the tubular extension and capable of moving between a first proximal position and a second distal position within said tubular extension,*

*said drive member having an arm pivotally attached by a pin and hole attachment to said movable end effector, said arm having a distal-most end surface for transferring force directly to said movable end effector causing said movable end effector to rotate about said pivot toward said longitudinal axis.*

* * * * *